United States Patent [19]

Gupta et al.

[11] 4,259,440
[45] Mar. 31, 1981

[54] HYDROLYSIS AND ASSAY OF TRIGLYCERIDES

[75] Inventors: Surendra K. Gupta; Panna R. Chaudhari, both of Elkhart, Ind.

[73] Assignee: Miles Laboratories, Inc., Elkhart, Ind.

[21] Appl. No.: 40,559

[22] Filed: May 21, 1979

[51] Int. Cl.³ .......................... C12Q 1/48; C12Q 1/44
[52] U.S. Cl. ........................................ 435/15; 435/19; 435/26; 435/42; 435/805; 435/810
[58] Field of Search ...................... 435/11, 15, 19, 26, 435/805, 42, 810

[56] References Cited

U.S. PATENT DOCUMENTS

| | | | |
|---|---|---|---|
| 3,703,591 | 11/1972 | Bucolo | 435/19 |
| 3,759,793 | 9/1973 | Stork | 435/19 |
| 3,862,009 | 1/1975 | Wahlefeld | 435/15 |
| 3,898,130 | 8/1975 | Komatsu | 435/19 |
| 3,925,164 | 12/1975 | Beaucamp | 435/11 |
| 4,045,297 | 8/1977 | Weelas | 435/19 |
| 4,056,442 | 11/1977 | Huang | 435/19 |
| 4,066,508 | 1/1978 | Rauscher | 435/19 |

*Primary Examiner*—Ernest G. Therkorn
*Attorney, Agent, or Firm*—James D. McNeil

[57] ABSTRACT

A method and composition for the hydrolysis and assay of triglycerides are disclosed. The method includes the steps of adding lipase and cholesterol esterase to a triglyceride in combination with a glycerol assay system and determining the amount of triglycerides present based on the amount of glycerol produced. The composition includes a mixture of lipase, cholesterol esterase and a glycerol assay system.

20 Claims, No Drawings

HYDROLYSIS AND ASSAY OF TRIGLYCERIDES

BACKGROUND OF THE INVENTION AND PRIOR ART

Determination of serum triglyceride levels in mammalian blood is of importance because elevated levels may be useful in the diagnosis of certain maladies. For example, determination of serum triglycerides is used to screen for coronary artery diseases, diabetes mellitus, nephrosis, biliary obstruction and various metabolic disorders caused by endocrine disturbances.

Triglycerides have the general structural formula shown in the following equation:

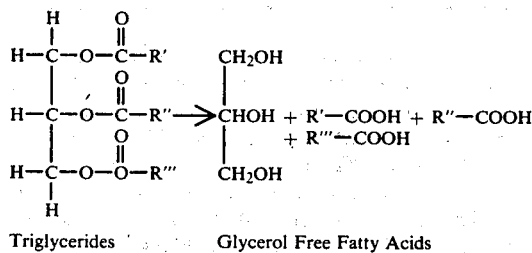

Triglycerides      Glycerol Free Fatty Acids

Determination of triglyceride levels is carried out by splitting the triglyceride as indicated above, to liberate free fatty acids (FFA) and glycerol.

Early procedures for liberation of glycerol and FFA involved saponification by addition of an alcoholic solution of alkali metal hydroxide. The procedures required arduous and time-consuming steps, such as the use of elevated temperatures, removal of materials such as phospholipids, glucose and bilirubin, deproteinization and neutralization with acid.

The number of triglyceride determinations performed in clinical laboratories has steadily increased in the past three years, producing a demand for a rapid method of liberation of glycerol and determination of triglycerides. Therefore, totally enzymatic methods for triglyceride determination have rapidly gained in favor. These methods involve the sequence of enzymatic hydrolysis of triglycerides followed by enzymatic determination of the glycerol liberated. For a review of the principles involved, see *Clin. Chem.* 19, 476 (1973) and 21, 1627 (1975).

One of the first approaches used in the enzymatic hydrolysis of triglycerides involved the use of animal source enzymes, e.g., pancreatic lipase, isolated from beef pancreas. The enzyme was unsatisfactory because of the incomplete hydrolysis of the triglycerides into glycerol; incomplete hydrolysis results in a mixture of mono and diglycerides. The use of microbial source lipase was then investigated. Again, because of problems with incomplete hydrolysis, unsatisfactory results were obtained. Consequently, research to improve enzymatic hydrolysis was undertaken by numerous laboratories. This research interest is reflected in the patents referred to below.

U.S. Pat. No. 3,703,591 discloses an enzymatic method for hydrolysis of triglycerides which involves adding to the triglycerides a mixture of lipase and a protease. The presence of protease causes a reduction in the stability of the enzyme test system.

U.S. Pat. No. 3,898,130 discloses an enzymatic method for hydrolysis of triglycerides which involves the use of a combination of a lipase and a bile salt, such as sodium taurodeoxycholate.

U.S. Pat. No. 4,056,442 discloses an enzymatic method for hydrolysis of triglycerides which involves the use of two microbial lipases, obtained from *Rhizopus arrhizus* and *Candida cyclindracea*, to overcome some of the disadvantages of the above-described lipase-containing mixtures. The amount of lipase required is a significant disadvantage; approximately 70 units of *R. arrhizus* and 64 units of *C. cylindracea* are required for complete hydrolysis.

U.S. Pat. No. 3,862,009 discloses an enzymatic method for hydrolysis of triglycerides which involves the use of a lipase from *R. arrhizus*, carboxyl esterase and an alkali metal or alkaline earth metal alkyl sulfate of 10–15 carbon atoms. The carboxyl esterase is specific for the hydrolysis of lower fatty acid esters, such as methyl or ethyl butyrate, whereas cholesterol esterase is specific for the hydrolysis of steroid esters.

U.S. Pat. No. 4,066,508 discloses an enzymatic method for hydrolysis of triglycerides which involves adding a polyglycol to the composition claimed in the '009 patent.

None of the patents discussed above disclose or suggest an economical composition and rapid method for triglyceride determination by use of an enzymatic composition of lipase and cholesterol esterase.

SUMMARY OF THE INVENTION

The present invention is directed to a method and composition for determining the amount of triglycerides present in an aqueous fluid. The method comprises contacting the fluid with a mixture of a lipase and cholesterol esterase for a time sufficient to hydrolyze the triglyceride to glycerol and free fatty acids and determining the amount of triglycerides present based on the amount of glycerol produced. The composition of the present invention for the determination of triglycerides comprises a mixture of a lipase, cholesterol esterase and a glycerol assay system.

The glycerol produced by splitting the triglyceride molecule can be measured by various methods known to those skilled in the art.

DESCRIPTION OF THE INVENTION

The enzymatic hydrolysis of the triglycerides according to the present invention can be carried out at a pH of from 6 to 9; preferably the pH is from 7 to 8. The enzymatic hydrolysis can be carried out at a temperature of from 20° to 60° C., depending on the stability characteristics of the lipase and cholesterol esterase enzymes. Preferably the temperature is from 30° to 40° C.

Any buffer can be used in the enzymatic hydrolysis which is effective to maintain the above pH range. Suitable buffers include tris(hydroxylmethyl)amino methane; triethanol amine, imidazole, glycine, borate, and collidine.

A surfactant is advantageously added to the enzymatic hydrolysis mixture to increase the stability of the hydrolysis mixture. Suitable surfactants include sodium cholate and sodium taurocholate.

The cholesterol esterase employed in the present invention can be obtained from suitable microorganisms, such as microorganisms of the Pseudomonas, Candida and Streptomyces genus. Cholesterol esterase from *Pseudomonas aeruginosa* is preferred because of its high stability at elevated temperatures. The cholesterol esterase can be obtained from animal sources such as beef pancreas.

The lipase employed in the present invention can be obtained from any suitable microorganism, such as *Rhizopus delemar, Phizopus arrhizus, Chromobacterium viscosum, Aspergillus niger, A. flavus oryzae, Candida lipolytica, C. cylindracea, Mucor miehei, M. pusillus* or *M. lipolyticus,* or from animal sources, such as beef pancreas. The lipase from *C. viscosum* or from *R. delemar* is preferred.

One skilled in the art can easily determine the optimum amount of cholesterol esterase for achievement of 100% hydrolysis of triglycerides by the procedures described.

A range of from about 0.01 to 5.0 U of cholesterol esterase per 10 U lipase is effective for hydrolyzing triglyceride samples. A preferred range is from about 0.35 to 1.3 U of cholesterol esterase per 10 U lipase.

As used hereinafter, one unit of lipase is defined as the amount of enzyme capable of catalyzing the release of 1 $\mu$mole of fatty acid per minute at 37° C. using olive oil as the substrate, under the specific assay conditions described below.

LIPASE ASSAY

In a 250 ml flask, a reaction mixture of 2.0 ml of olive oil; 9 ml of 0.1 M potassium phosphate buffer (pH 7.0); 0.1 ml of 0.1 M $CaCl_2$ solution, and 0.05 ml of 20% albumin containing 0.2% sodium azide solution was incubated at 37° C. for about 10 minutes until the reaction mixture reached 37° C. A 0.1 ml portion of lioase (0.5 mg/ml) solution was added and stirred at 400 rpm, at 37° C. for 30 minutes. A 40 ml portion of 95% ethanol was poured into the mixture. The amount of fatty acids produced was determined by titration with 0.05 N KOH solution. The units of lipase activity were calculated as follows:

$$\text{enzyme activity in U/mg} = \frac{\text{Normality of KOH} \times \text{volume of KOH} \times 10^3}{30 \times \text{mg of lipase in reaction}}$$

One unit of cholesterol esterase is defined as the amount of enzyme capable of catalyzing the release of 1 $\mu$mole of cholesterol per minute at 37° C. using a "cholesterol concentrate" material as the substrate, under the specific assay conditions described below.

The "cholesterol concentrate" used was a solution of lipo-proteins derived from bovine serum, containing approximately 1000 mg percent cholesterol; 75±5 percent was in the form of cholesterol esters and 25±5 percent was in the form of free cholesterol. The cholesterol concentrate is commercially available from Miles Laboratories, Inc., Elkhart, Ind.

CHOLESTEROL ESTERASE ASSAY

In a 250 ml flask, a reaction mixture (designated "mixture A") was prepared by adding to 90 ml of distilled water the following: 1.497 g ($KH_2PO_4$); 1.568 g $K_2HPO_4$; 0.431 g. sodium cholate; 1.05 ml of a 25% solution of an alkylphenoxypolyethoxy ethanol, commercially available from Rohm and Haas Co., Philadelphia, Pa., under the trade designation Triton X-100; 0.0169 g 4-aminoantipyrine (used as a chromogen); and 0.145 ml phenol (10 M). Sufficient distilled water was added to make a final volume of 100 ml.

A solution of peroxidase, commercially available from Miles Laboratories, Inc., Elkhart, Ind., having an activity of 60 U/mg, was prepared by dissolving 4 mg in 1 ml distilled water. Cholesterol oxidase, commercially available in a liquid form from Miles Laboratories, Inc., having an activity of 10 U/ml was used.

The cholesterol esterase being assayed should be employed in a concentration of about 1.0 to 1.5 U/ml. The activity of the cholesterol esterase was determined by measuring the change in optical density at 500 nanometers as follows:

Into a 10 mm cell, the following were placed:

|  | Test |
|---|---|
| "Mixture A" | 2.9 ml |
| Cholesterol Oxidase | 0.05 ml |
| Peroxidase | 0.03 ml |
| Cholesterol Concentrate | 0.05 ml |

The cell was incubated at 37° C. for approximately 10 minutes, until a constant 37° C. was maintained. A 0.025 ml portion of the cholesterol esterase solution being assayed was then added to the test cell. The increase in absorbance ($\Delta A_s$) at 500 nm was measured for approximately 1-3 minutes and recorded on a continuous recorder. The increase in absorbance should range between 0.030-0.060 per minute. As a blank control, the cholesterol produced by hydrolysis of cholesterol concentrate in the absence of cholesterol esterase was determined by measuring the increase in absorbance ($\Delta A_c$) for approximately 1-3 minutes and recorded on a continuous recorder. A plot of the optical density vs. time was prepared for the sample and for the blank. Using the linear portion of the curves obtained, the activity of the cholesterol esterase was calculated as follows:

$$\text{enzyme activity in U/mg} = (\Delta A_s/\text{min} - \Delta A_c/\text{min}) \times \frac{1}{5.33} \times \frac{3.055}{0.25} \times \frac{10}{1}$$

(The molar absorption coefficient for the oxidized chromogen produced is $5.33 \times 10^3$)

METHODS FOR GLYCEROL DETERMINATION

The glycerol produced by enzymatic splitting of the triglyceride molecule with the mixture of lipase and cholesterol esterase can be measured by various glycerol assay systems known to those skilled in the art. One enzymatic glycerol assay system involves the use of the enzymes glycerol kinase (GK), pyruvate kinase (PK), and lactate dehydrogenase (LDH), and the compounds adenosine triphosphate (ATP), phosphoenolpyruvic acid (PEP) and reduced nicotinamide adenine dinucleotide (NADH). The glycerol is converted to $\alpha$-glycerol phosphate and the ATP is converted to adenosine diphosphate (ADP) by GK. The diphosphate is converted back to the triphosphate with the simultaneous conversion of PEP to pyruvate by PK. The pyruvate is converted to lactate with the simultaneous conversion of NADH to oxidized nicotinamide adenine dinucleotide (NAD), by LDH. As conversion of the glycerol proceeds, the optical density of the mixture at 340 nanometers decreases as a result of the oxidation of NADH to NAD. The change in optical density is directly proportional to the amount of glycerol produced. The amount of triglycerides present is calculated as described in Example 1 hereinafter. The reaction can be illustrated as follows:

Triglyceride + Lipase + Cholesterol Esterase ⟶ Glycerol + FFA     1.

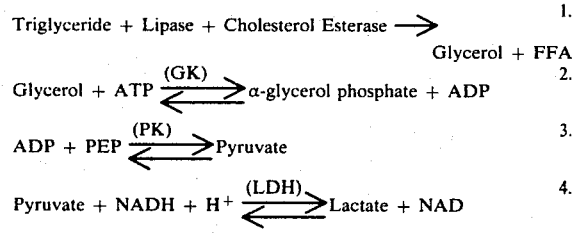

A second enzymatic glycerol assay system involves the use of the enzymes glycerol kinase (GK) and α-glycerolphosphate dehydrogenase (α-GPDH) and the compounds ATP and NAD. The glycerol is converted to α-glycerol phosphate and the ATP is converted to ADP by glycerol kinase. The α-glycerol phosphate is converted to dihydroxy acetone phosphate with the simultaneous conversion of NAD to NADH by α-GPDH. The NADH can be coupled to a dye in the presence of a diaphorase. Reduction of the dye can be followed on a conventional colorimeter. The amount of glycerol present can be determined by measuring the amount of color produced, and the amount of triglycerides present calculated as described in Example 2 hereinafter. Optionally, the amount of glycerol present can be determined by measuring the increase in optical density of the reaction mixture at 340 nanometers as a result of the reduction of NAD to NADH.

The reaction can be illustrated as follows:

Triglyceride + Lipase + Cholesterol Esterase ⟶ Glycerol + FFA

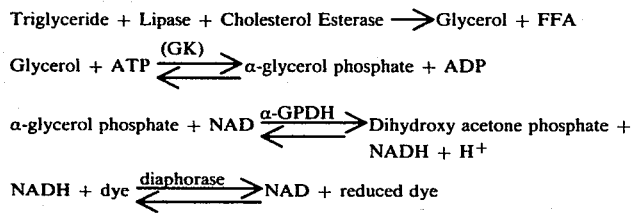

A third enzymatic glycerol assay system involves the use of glycerol oxidase (GLO). The glycerol is converted to glyceraldehyde, with the liberation of $H_2O_2$. The $H_2O_2$ can be measured by adding a reduced chromogen and peroxidase and measuring the amount of oxidized chromogen formed, based on a color change.

The reaction can be illustrated as follows:

Triglyceride + Lipase + Cholesterol Esterase ⟶ Glycerol + FFA     1.

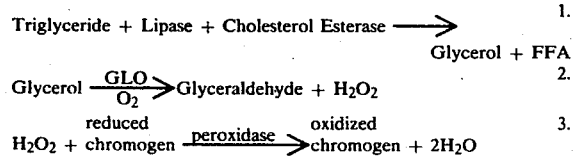

A fourth enzymatic glycerol assay system involves the use of NAD and glycerol dehydrogenase (GD). Dihydroxyacetone is formed, with the simultaneous reduction of NAD to NADH. Again, the NADH can be measured directly or coupled with a dye and a diaphorase as described previously.

A preferred reagent composition suitable for the hydrolysis of triglycerides and assay of triglycerides in a sample was prepared as described below.

EXAMPLE 1

A. Hydrolysis Mixture

The hydrolysis mixture was prepared by dissolving 0.25 mg of lipase which contained 120 U and 1 mg of cholesterol esterase containing 10.7 U in 1 ml of 0.01 M tris(hydroxymethyl)amino methane adjusted to a pH of 8.0 with hydrochloric acid. The tris compound is commercially available from Sigma Chemical, St. Louis, Mo., under the trade designation Trizma Base. To the above, 10 μmoles of sodium cholate was added.

The lipase and cholesterol esterase used herein were free of proteases. For each test, as described hereinafter, 30 μl of the above solution was used, containing 3.6 U of lipase and 0.32 U of cholesterol esterase; (0.88 U cholesterol esterase per 10 U lipase.)

The lipase was obtained from Calbiochem, LaJolla, Calif., derived from the R. delemar microorganism. The cholesterol esterase was obtained from Miles Laboratories, Inc., derived from P. aeruginosa.

B. Glycerol Assay System

An assay reagent system for the detection of glycerol was prepared by dissolving in 90 ml 0.1 M potassium phosphate buffer at a pH of 7.0:

| | |
|---|---|
| Phosphoenolpyruvate (PEP) | 10.3 mg |
| Adenosine triphosphate (ATP) | 18.2 mg |
| Pyruvate Kinase (PK) | 400 units |
| Lactate dehydrogenase (LDH) (animal) | 140 units |

1.

2.

3.

4.

| | |
|---|---|
| NADH | 19.0 mg |
| Magnesium sulfate | 49.3 mg |

(Magnesium salts such as magnesium sulfate and magnesium acetate are essential for the activation of glycerol kinase).

A sufficient quantity of 0.1 M phosphate buffer, pH 7.0, was added to give a volume of 100 ml. A 0.95 ml portion of the assay mixture, 30 μl of the hydrolysis mixture and 20 μl of a triglyceride sample (which was a human serum sample obtained from a hospital), were dispensed into a 1.2 ml cuvette. The cuvette was placed in a constant temperature water bath at 30° C. for 5 minutes until the reaction mixture equilibrated at 30° C.

The NAD produced was measured spectrophotometrically at 340 nm wavelength, and the triglyceride present determined, based on the amount of glycerol produced, as follows:

The initial absorbance ($A_0$) was read at 340 nm and 20 μl of glycerol kinase solution (664 U/100 ml) was added. Simultaneously the solution was mixed by inverting the cuvette with a film over the cuvette mouth. After a timed mixing period of 12 minutes, the final absorbance was read ($A_{12}$). The blank rate due to the triglyceride sample was determined by measuring the change in absorbance between 12 and 24 minutes after the addition of glycerol kinase. The following calculations were carried out.

The $\Delta A_{12}$, the change in absorbance, was obtained by subtracting the final absorbance ($A_{12}$) from the initial absorbance ($A_0$).

The blank $\Delta_{24}$, the change in absorbance due to the hydrolyzed triglyceride sample, was obtained by subtracting the final absorbance ($A_{24}$) from the absorbance ($A_{12}$).

The $\Delta A$, corrected for the blank, was obtained by subtracting the blank ($\Delta A_{24}$) from the $\Delta A_{12}$ value. The amount of triglycerides present was then calculated as follows:

$$\frac{mg/100\ ml}{triglycerides} = \frac{\Delta A \times 885.4 \times total\ volume \times 100}{6.22 \times sample\ volume \times 1000} = \frac{138.1}{mg/100\ ml}$$

In order to determine the accuracy of the method, the hospital serum sample used above was tested by using a kit commercially available from Calbiochem under the trade designation Stat Pack. A triglyceride value of 140 mg/100 ml was obtained. The procedure used with the kit involves enzymatic hydrolysis and is described in *Clin. Chem.* 22, 1896–1899 (1976) as being accurate and meeting the Center for Disease Control criteria for precision determination of low, medium and high triglyceride concentration.

At a reaction temperature of 30° C., complete hydrolysis of the triglycerides was achieved in 12 minutes. The extent of hydrolysis was determined by plotting the change in optical density against time (in minutes). Completion of hydrolysis was verified by running a control sample.

In order to show non-criticallty of specific glycerol assay procedures, the experiment of Example 1 was repeated, using the glycerol kinase and α-glycerolphosphate dehydrogenase glycerol assay system previously described.

EXAMPLE 2

A glycerol assay system was prepared by dissolving in 90 ml 0.1 M tris buffer at a pH of 7.5:

| | |
|---|---|
| Magnesium chloride | 0.06 gm |
| Adenosine triphosphate (ATP) | 0.18 gm |
| Sodium chloride (NaCl) | 0.585 gm |
| Calcium chloride (CaCl$_2$) | 0.0555 gm |
| Ethylene diamine tetraacetic acid (EDTA) | 0.0186 gm |
| (NAD) Nicotinamide adenine dinucleotide | 0.072 gm |
| 2-(p-indophenyl-3-p-nitrophenyl-5 phenyl tetrazolium chloride | 0.025 gm |
| Diaphorase | 600 units |
| α-Glycerolphosphate dehydrogenase | 1400 units |

The above reaction mixture was diluted to 100 ml with 0.1 M tris buffer (pH 7.5).

A 0.95 ml portion of the assay mixture, 30 μl of the hydrolysis mixture of Example 1 (containing 3.6 U lipase and 0.32 U of cholesterol esterase) and 20 μl of the triglyceride sample containing 140 mg/100 ml triglycerides were dispersed into a 1.2 ml cuvette. The cuvette was placed in a constant temperature water bath at 37° C. for 5 minutes until the reaction mixture equilibrated at 37° C. A 20 μl portion of glycerol kinase solution (664 U/100 ml) was added. Simultaneously the solution was mixed by inverting the cuvette with film on the cuvette mouth. After a timed mixing period of 12 minutes, the final absorbance ($A_{12}$) at 500 nm wavelength was read. The blank rate was determined by measuring the change in absorbance using distilled water instead of the hydrolysis mixture. The amount of glycerol present was determined by the amount of color produced and the triglycerides present calculated as follows.

The $\Delta A$, corrected for the blank, was obtained by subtracting the blank ($\Delta_B$) from the final absorbance ($A_{12}$). The amount of triglycerides present was then calculated as follows:

$$\frac{mg/100\ ml}{triglycerides} = \frac{\Delta A \times 885.4 \times total\ volume \times 100}{19.3 \times sample\ volume \times 1000} = 136$$

In order to determine the amount of lipase and cholesterol esterase necessary for the optimum hydrolysis improvement, a comparative study was undertaken.

EXAMPLE 3

A lipase-cholesterol esterase mixture was prepared as described in Example 1, having varying concentrations of cholesterol esterase present along with the glycerol assay system of Example 1. The mixtures were then used to assay glycerol in a triglyceride standard, as summarized in Table I:

TABLE I

| | Cholesterol Esterase (P. aeruginosa) | | | |
|---|---|---|---|---|
| Lipase (R. delemar) (U/Test) | (U/Test) | (U/10 U Lipase) | % Hydrolysis in 8 min. | Time Required for 100% Hydrolysis |
| 1. 3.6 | 0.16 | 0.44 | 77 | 17 min. |
| 2. 3.6 | 0.32 | 0.88 | 90 | 12 min. |
| 3. 3.6 | 0.48 | 1.33 | 100 | 8 min. |
| 4. 3.6 | 0.64 | 1.78 | 94 | 9 min. |
| 5. 3.6 | 0 | — | 31 | Amount of hydrolysis was unchanged at 60 min. |
| 6. 0 | 0.32 | — | 29 | Amount of hydrolysis was unchanged at 60 min. |

It is obvious from Table I that the presence of cholesterol esterase enhances the extent of triglyceride hydrolysis and thus reduces the amount of time required for testing of triglycerides.

The test compositions and methods described in Examples 1–3 used lipase derived from the microorganism *R. delemar* and cholesterol esterase derived from *P. aeruginosa*. In order to demonstrate that a mixture of lipase and cholesterol esterase obtained from sources other than *R. delemar* and *P. aeruginosa* respectively can be used, the following experiments were conducted using other sources of the enzymes.

EXAMPLE 4

The procedure of Example 1 was followed wherein lipase and cholesterol esterase were mixed together and dissolved in a tris(hydroxymethyl)amino methane buffer solution. The lipase and cholesterol esterase sources and concentrations are described in Table II below.

The test results in Table II again demonstrate that addition of cholesterol esterase to a lipase significantly decreases the amount of time required for hydrolysis, or significantly increases the extent of hydrolysis. These test results also demonstrate that the source of the lipase and cholesterol esterase is not a critical limitation.

TABLE II

| Lipase (Source) | Lipase (Amount) | Cholesterol Esterase (Source) | Cholesterol Esterase U/Test | Cholesterol Esterase U/10 U Lipase | Time Required for Complete Hydrolysis |
| --- | --- | --- | --- | --- | --- |
| *Chromobacterium viscosum* | 9U | *P. aeruginosa* | 0.32U | 0.35 | 7-8 minutes |
| *Chromobacterium viscosum* | 9U | *P. aeruginosa* | 0 | — | 14 minutes |
| *R. delemar* | 3.6 | Beef pancreas | 0.48U | 1.3 | 8 minutes |
| *R. delemar* | 3.6 | Beef pancreas | 0 | — | Incomplete Hydrolysis |

The lipase and cholesterol esterase-containing composition of the present invention not only hydrolyzes triglycerides, it also hydrolyzes cholesterol esters present and therefore can be used for the determination of both triglycerides and cholesterols in conjunction with a glycerol assay system and cholesterol assay system.

Tests have been conducted to determine the stability of mixtures of dry lipase and cholesterol esterase. Examination of mixtures which have been stored for up to 45 days at 50° C. indicate no loss in activity of either compound. The above description involved a liquid phase system for assaying triglycerides. The composition and method of the present invention can also be employed in a solid phase device. The device is prepared, for example, by impregnating a carrier with a solution of a lipase, cholesterol esterase and a glycerol assay system and thereafter drying the impregnated carrier. For example, a carrier can be impregnated with lipase, cholesterol esterase and the glycerol assay system of Example 2, and dried. A fluid to be tested is then contacted with the device and the amount of triglycerides present determined, based on the amount of glycerol produced.

What is claimed is:

1. A method for determining the amount of triglycerides present in an aqueous fluid which comprises contacting the fluid with a mixture of a lipase and cholesterol esterase for a time sufficient to hydrolyze the triglyceride to glycerol and free fatty acids and determining the amount of triglycerides present based on the amount of glycerol produced.

2. A method as claimed in claim 1 wherein the lipase is produced by a microorganism selected from the group consisting of *Rhizopus delemar*, and *Chromobacterium viscosum*.

3. A method as claimed in claim 1 wherein the cholesterol esterase is obtained from the microorganism *Pseudomonas aeruginosa* or from beef pancreas.

4. A method as claimed in claim 1 wherein the lipase is produced from a microorganism selected from the group consisting of *Rhizopus delemar, Rhizopus arrhizus* and *Chromobacterium viscosum* and the cholesterol esterase is obtained from the microorganism *Pseudomonas aeruginosa* or from beef pancreas.

5. A method as claimed in claim 1 wherein the amount of glycerol present is determined enzymatically.

6. A method as claimed in claim 1 wherein the hydrolysis is carried out at a pH of from 6 to 9 and a temperature of from 20° to 40° C.

7. A method as claimed in claim 1 wherein a buffer is added to the mixture of lipase and cholesterol esterase.

8. A method as claimed in claim 1 wherein a surfactant is added to the mixture of lipase and cholesterol esterase.

9. A method as claimed in claim 1 wherein the fluid is a body fluid.

10. A method as claimed in claim 9 wherein the body fluid is serum or plasma.

11. A method as claimed in claim 1 wherein there is present from 0.01 to 5.0 U cholesterol esterase per 10 U lipase.

12. A method as claimed in claim 1 where there is present from 0.35 to 1.8 U cholesterol esterase per 10 U lipase.

13. A method as claimed in claim 1 wherein the amount of glycerol present is determined by contacting the liberated glycerol with a glycerol assay system comprising: adenosine triphosphate; phosphoenolpyruvate; pyruvate kinase; lactate dehydrogenase; reduced nicotinamide adenine dinucleotide; glycerol kinase and a magnesium salt.

14. A method as claimed in claim 1 wherein the amount of glycerol present is determined by contacting the liberated glycerol with a glycerol assay system comprising: adenosine triphosphate; glycerol kinase; α-glycerolphosphate dehydrogenase; oxidized nicotinamide adenine dinucleotide; diaphorase and a dye.

15. A composition for the determination of triglycerides by enzymatic hydrolysis comprising a mixture of lipase, cholesterol esterase and a glycerol assay system.

16. A composition as claimed in claim 15 wherein there is present a buffer.

17. A composition as claimed in claim 15 wherein there is present a surfactant.

18. A composition as claimed in claim 15 wherein the assay system comprises: adenosine triphosphate; phosphoenolpyruvate; pyruvate kinase; lactate dehydrogenase; reduced nicotinamide adenine dinucleotide; glycerol kinase and a magnesium salt.

19. A composition as claimed in claim 15 wherein the assay system comprises: adenosine triphosphate; glycerol kinase; α-glycerol phosphate dehydrogenase; oxidized nicotinamide adenine dinucleotide; diaphorase and a dye.

20. A test device for the determination of triglycerides in a fluid which comprises a carrier incorporated with lipase, cholesterol esterase and a glycerol assay system.

* * * * *